United States Patent [19]

Gallagher et al.

[11] Patent Number: 5,219,646

[45] Date of Patent: Jun. 15, 1993

[54] POLYESTER BLENDS AND THEIR USE IN COMPOSTABLE PRODUCTS SUCH AS DISPOSABLE DIAPERS

[75] Inventors: Francis G. Gallagher; Hyunkook Shin; Raymond F. Tietz, all of Wilmington, Del.

[73] Assignee: E. I. Du Pont de Nemours and Company, Wilmington, Del.

[21] Appl. No.: 834,791

[22] Filed: Feb. 13, 1992

Related U.S. Application Data

[63] Continuation-in-part of Ser. No. 769,417, Oct. 1, 1991, abandoned, which is a continuation-in-part of Ser. No. 645,849, Jan. 25, 1991, Pat. No. 5,097,004, and Ser. No. 645,995, Jan. 25, 1991, Pat. No. 5,097,005, and Ser. No. 522,134, May 11, 1990, Pat. No. 5,053,482.

[51] Int. Cl.$^5$ .................... B32B 27/34; B32B 27/36; C08F 20/00
[52] U.S. Cl. .................... 428/287; 428/481; 428/532; 525/437; 604/370; 604/372; 521/916
[58] Field of Search ............... 428/286, 287; 604/370, 604/372; 528/272, 295, 301, 302, 308.6; 525/437, 450, 471

[56] References Cited

U.S. PATENT DOCUMENTS

| 3,018,272 | 1/1962 | Griffing et al. | 260/75 |
|---|---|---|---|
| 3,853,820 | 12/1974 | Vachon | 260/75 |
| 4,016,117 | 4/1977 | Griffin | 523/128 |
| 4,021,388 | 3/1977 | Griffin | 523/128 |
| 4,125,495 | 11/1978 | Griffin | 260/174 |
| 4,218,350 | 8/1980 | Griffin | 264/331 |
| 4,324,709 | 4/1972 | Griffin | 523/52 |
| 4,418,116 | 11/1983 | Scott | 428/288 |
| 4,420,576 | 12/1983 | Griffin | 524/47 |
| 4,483,976 | 11/1984 | Yamamoto et al. | 528/275 |
| 4,526,738 | 7/1985 | Miyoshi et al. | 264/176 |
| 4,704,329 | 11/1987 | Hancock et al. | 428/369 |
| 4,883,706 | 11/1989 | Grosjean | 428/215 |
| 5,097,005 | 3/1992 | Tietz | 528/272 |

FOREIGN PATENT DOCUMENTS 0327505 1/1989 European Pat. Off. .
0388924 3/1990 European Pat. Off. .

OTHER PUBLICATIONS

Ingamells, J. Appl. Poly. Sci., vol. 26, 4087–4101 (1981).
Grassie, Developments in Polymer Degradation-5, 112–119 (1984), Applied Science Publishers.
Nishiyamaet al, "Biodegradable Plastics Utilizing Biomass", Kogyo Zairyo 38, No 1: 47–52 (1990).
Roper et al, "The Role of Starch in Biodegradable Thermoplastic Materials", Starch, 42, 123–130 (1990).

*Primary Examiner*—George F. Lesmes
*Assistant Examiner*—Chris Raimund

[57] ABSTRACT

The invention provides novel blends of starch with polyesters, and shaped articles of such blends, including fibers, foams and films, nonwovens from the fibers and disposable products such as diapers. The products are degradable under the conditions typically existing in waste composting processes, have low ingredient costs and yet provide strength and toughness properties adequate for end uses such as in disposable diapers. The polyesters are based upon polyethylene terephthalate copolymerized with other ingredients, including non-aromatic diacids, such as adipic and glutaric acids, polyethylene ether groups, such as diethylene glycol or higher polyalkylene glycols, and hydroxy acids.

10 Claims, No Drawings

POLYESTER BLENDS AND THEIR USE IN COMPOSTABLE PRODUCTS SUCH AS DISPOSABLE DIAPERS

CROSS-REFERENCE TO RELATED APPLICATIONS

This application is a continuation-in-part of our copending application Ser. No. 07/769,417, filed Oct. 1, 1991, now abandoned which is itself a continuation-in-part of the copending application filed by Gallagher et al as Ser. No. 07/645,849, now U.S. Pat. No. 5,097,004 and of the copending application filed by Tietz as Ser. No. 07/645,995, now U.S. Pat. No. 5,097,005 both filed Jan. 25, 1991, and a continuation-in-part of copending parent application Ser. No. 07/522,134, filed by Tietz, May 11, 1990, now U.S. Pat. No. 5,053,482.

FIELD OF THE INVENTION

This invention relates to novel blends of polyesters to their processing and to products therefrom. The blends are with starch. The products include fibers, films, foams, coated papers, extruded nets, molded objects and nonwovens and disposable products such as diapers from such products. The products disintegrate quickly and are degradable to innocuous materials under conditions used in municipal solid waste composting systems.

BACKGROUND OF THE INVENTION

The inadequate treatment of municipal solid waste which is being put in landfills and the increasing addition of nondegradable materials, including plastics, to the municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bags, and numerous other products. The composting of non-recyclable solid waste is a recognized and growing method of reducing solid waste volume for landfilling and/or making a useful product from the waste to improve the fertility of fields and gardens. One of the limitations to marketing such compost is the visible contamination by undegraded plastic such as film and fiber fragments.

As related in the aforesaid parent applications, which are hereby specifically incorporated herein by reference, there was a desire to achieve several objectives, as follows:

1-to provide components which are useful in disposable products and which are degraded into less contaminating forms under the conditions typically existing in waste composting processes. These conditions may involve temperatures no higher than 70° C., and averaging more nearly 55°-60° C., humid conditions as high as 100% relative humidity, and exposure times which range from two weeks to more than three months.

2-to provide disposable components which will not only degrade aerobically/anaerobically in composting, but will continue to degrade in the soil or landfill. As long as water is present, they will continue to break down into low molecular weight fragments which can be ultimately biodegraded by microorganisms completely into biogas, biomass and liquid leachate, as for natural organics like wood.

3-to provide novel polyesters for making the aforementioned fibers, films, coatings and nonwoven sheets of the polyesters, and disposable diapers containing the nonwoven sheets.

4-to provide polyesters and derivative products which have low ingredient costs and yet provide strength and toughness properties adequate for end uses such as in disposable diapers.

Accordingly, as described therein, useful novel degradable polyesters were provided and fibers, nonwoven sheet, films and combinations thereof, and disposable diapers comprising such materials. It would, however, be desirable to provide further improvements and additional degradable materials, having regard to the public interest in this area.

Abbreviations and nomenclature herein, except as otherwise indicated, are as described in aforesaid U.S. Pat. No. 5,053,482, and applications Ser. Nos. 07/645,849 and 07/645,995, and application Ser. Nos. 07/769,414 and 07/771,019 filed Oct. 1, 1991, to cover further novel degradable polyesters and their products, which hereby incorporated herein by reference, as are applications Ser. Nos. 07/834,795, 07/834,796, 07/834,794, 07/834,793, 07/834,797, and 07/834,792, all filed Feb. 13, 1992.

DESCRIPTION OF RELATED ART

Various polyester compositions have been suggested in the past for biodegradable end uses. These include polyhydroxybutyrate, polyactide, polycaprolactone, polyglycolide, and their copolymers. They have not been widely adopted in high volume uses, however, because they are either too expensive or their properties are inadequate for the uses mentioned above.

It is known to use salts of 5-sulfoisophthalic acid and its esters as comonomers to improve acid dyeability of polyethylene terephthalate fibers, see for example U.S. Pat. No. 3,018,272 (Griffing et al.). Moreover, this type of fiber is known to have an increased rate of hydrolytic degradation, see for example J. Appl. Poly. Sci., vol. 26, 4087-4094 (W. Ingamells et al.) and Developments in Polymer Degradation 5, edited by N. Grassie, Applied Science Publishers, 1984, pages 112-119. The use of 5-sulfoisophthalate salts together with other neutral comonomers has been disclosed to increase dye rates, but the proportion of the neutral comonomer is usually minimized to affect physical properties as little as possible, see for example U.S. Pat. Nos. 4,704,329 (Hancock et al.) and 3,853,820 (Vachon).

It is also known to use as much as 20 to 45 mole % diethylene glycol as a comonomer with ethylene glycol and terephthalic to provide polyesters having suitable melting and bonding characteristics for a nonwoven binder fiber, see for example U.S. Pat. No. 4,418,116 (Scott). Further, it is known to prepare water dispersible papermaking binder fibers which are made containing 5 to 20 mole % of diethylene glycol and preferably more than 3 mole % 5-sulfoisophthalate, see for example U.S. Pat. No. 4,483,976 (Yamamoto et al.). In the latter patent each of the specific polymers disclosed contain 7 mole % or more of the 5-sulfoisophthalate salt.

There are also references to uses of starch. Some of these refer to starch in relation to biodegradable materials. Some of these references disclose particular modifications of starch that enhance biodegradability.

For instance, it has been suggested to blend synthetic thermoplastic polymers with a water-containing destructurized starch, see Lay, et al. EP A2 0327505. Blends containing up to 99.9 wt % destructurized starch are disclosed with the preferred range being 70–99.5 wt % destructurized starch. The blends form thermoplastic melts upon heating in a closed vessel and may be processed using conventional means for thermoplastic materials. In these materials the starch is plasticized by water, released from the granules, and thus forms a continuous phase.

Polymer compositions comprising a synthetic resin, a biodegradable substance (such as starch) and a substance which is autoxidized to yield a peroxide which attacks the carbon to carbon linkages in the resin are disclosed in Griffin U.S. Pat. Nos. 4,016,117, 4,021,388, 4,125,495, 4,218,350, 4,324,709, and 4,420,576. Blends described therein are reported to "degrade to destruction typically within 12 months" when buried in soil.

Other references to biodegradable functionality involving starch include Aronoff et al EP A2 0388924, Nishiyana et al "Biodegradable Plastics Utilizing Biomass", Kogyo Zairyo 38, no. 1: 47–52 (1990) and Roper et al "The Role of Starch in Biodegradable Thermoplastic Materials," Starch, 42, 123–130 (1990).

SUMMARY OF THE INVENTION

The present invention is based on the finding that one can make blends from starch and the aforesaid novel degradable polyesters, and that such blends can be made and processed at practical temperatures to make useful shaped articles, such as fibers, films, etc. The resulting articles have the useful capability of disintegrating quickly and conveniently when subjected to appropriate compost conditions, by way of example.

In one embodiment of the invention there is, accordingly, provided a novel fiber and film forming blend of starch, in amount by weight 1 to 80%, and of a polyester, in amount by weight 99 to 20%, wherein said polyester consists essentially of recurring structural units of the formulae:

$$-[-C(O)-R-C(O)-OGO-]_a-[-C(O)-Q-O-]_b-$$

wherein up to about 40 mole % of R is selected from the group consisting of a chemical bond and one or more divalent, non-aromatic, $C_1-C_{10}$ hydrocarbylene radicals, and the remainder of R is at least about 85 mole % p-phenylene radical, wherein G is up to about 30 mole % of a polyethylene ether radical selected from the group consisting of $-(CH_2)_2-O-(CH_2)_2-$ and
$-(CH_2)_2-O-(CH_2)_2-O-(CH_2)_2-$ and the remainder of G is selected from the group consisting of polyalkylene ether radicals of molecular weight at least about 250, and $-(CH_2)_2-$, $-(CH_2)_3-$, and $-(CH_2)_4-$ radicals, wherein Q is derived from an hydroxy acid of formula $$HO[-C(O)-Q-O-]_xH,$$

where x is an integer, such hydroxy acid having a melting point at least 5 C below its decomposition temperature, and Q is selected from the group consisting of a chemical bond and hydrocarbylene radicals $-(CH_2)_n-$, where n is an integer from 1 to 5, $-C(R')H-$, and $-C(R')HCH_2-$, wherein R' is selected from the group of $-CH_3$ and $-CH_2CH_3$, and wherein "a" and "b" are mole fractions of the polymer, and the mole fraction "a" may be 0.6 to 1 and, correspondingly, mole fraction "b" may be 0 to 0.4, and wherein about 0.1 to about 15 mole %, preferably about 0.1 to about 2.5 mole % of the polymer contains alkali metal or alkaline earth metal sulfo groups, especially about 1.5 to about 2 mole % of such groups.

If desired, some of the G may be a radical of a polyalkylene glycol of (number average) molecular weight (MW) at least about 250, as disclosed in copending application Ser. No. 07/645,849, e.g. polyethylene glycol (PEG).

It is suprising that useful blends can be made at all, considering what is known about the characteristics of starch and considering the properties of the novel degradable polyesters. Accordingly, other aspects of the invention include processes for making and processing the novel blends.

Other embodiments of the invention include fibers, foams, films and coatings of the above blends and nonwovens of the fibers. It is surprising that the blends can be processed into useful articles. Accordingly, other aspects of the invention include such processing of the blends and of intermediate products. The invention also contemplates disposable products, such as diapers, which contain an absorbent body portion, with, on at least one surface, a water permeable sheet comprising the blend, a water impermeable sheet comprising the blend, or a combination thereof.

Blends with minor amounts, up to about 15% based on total blend weight, of other degradable polymers may also be employed provided that the dispersability of the starch in the polymer blend is not adversely affected. For example, additions of 5–10% of of polyethylene adipate have been found to be useful in preparing certain blends of the current invention.

Polyester copolymers having a melting point below the degradation temperature of the starch are desired in order to prevent degradation of the starch during subsequent processing. Although the thermal degradation point of starch is about 220 C., higher temperatures may be tolerated in polymer dispersions (G. J. L. Griffin Chapter 16 "Biodegradable Fillers in Thermoplastics", Advances in Chemistry Series 134, American Chemical Society, Washington, D.C. (1974). It should, however, be pointed out that special pretreatment of starch (as prescribed in Griffin's patents referred to above) is not necessarily a prerequisite for making blends according to the present invention. It is also desirable that the polyester compositions themselves be degradable when subjected to composting or landfill conditions. Polyester compositions having glass transition temperatures no higher than temperatures of composting operations, which typically are less than about 70 C., are preferred. Therefore it is preferable that the chemical composition of the polyester copolymers be chosen such that the glass transition temperature is less than about 70 C., and more preferably less than 65 C.

According to the present invention, the polyester is blended with approximately 1–80 weight % starch, with preferred levels being 5–70 weight % starch. The precise amounts desired will depend to a large extent on the dimensions of the intended articles and their intended use.

To prepare an article of relatively large dimensions that will be easily disintegrated, it is disclosed in the art as preferable to use a volume % and particle size of starch which when dissolved or digested by microorganisms give a complete, or almost complete, pathway through the article. When the percolation threshold is met or exceeded, presumably the starch particles adjacent to the surface of the article are degraded followed by degradation of particles in the interior of the article to provide a porous structure throughout the article. This percolation threshold is approximately 30 volume % with corn starch.

The particle size of the starch granules may, however, limit some of the attainable physical dimensions of certain articles, such as the gauge of thin films and coatings and the diameter of fibers. To facilitate the preparation of thinner films and fibers the particle size of starches may be decreased by grinding and oversized particles may be removed by procedures such as air classification. In addition, starch granules may be modified by treatments such as pregelatinization in which concentrated starch/water slurries are dried quickly by drum drying, spray drying, foam heat or puff extrusion. The pregelatinized starch may be dried and optionally ground and classified to yield fine starch particles. Other biodegradable derivatives of starch may be treated similarly. These may be used in the products described herein but the cost of such derivatization must be considered versus any increase in disintegration rate versus additive content. If desired, a mixture of two or more starches may be used.

We have also successfully blended finely divided protein materials, derived, e.g., from corn, such as zein, with the novel degradable polyesters to provide useful blends, in addition to or instead of the starch in the blends. This can be advantageous in one sense, because they can be of especially small particle size. But some of these other materials have aesthetic characteristics that may prove undesirable for certain end uses. Other materials that are contemplated and may prove useful, likewise, include wood pulp and other degradable materials, such as are mentioned, for example by Coughlin et al, in U.S. Pat. No. 4,480,061.

As indicated in the aforesaid applications, polyesters, for example derived from non-aromatic dibasic acids, such as adipic acid (abbreviation 6) and glutaric acid (abbreviation 5), as well as from terephthalic acid (abbreviation T), a metal salt of a 5-sulfoisophthalic acid (abbreviation 5SI), ethylene glycol (abbreviation 2G) or other lower alkylene glycol (such as 3G and 4G), and polyethylene ether glycols (abbreviations DEG or TEG), and, if desired, a $C_2$-$C_4$ polyalkylene ether glycol of the indicated higher molecular weight (such as PEG), undergo degradation when subjected to the conditions of moisture and temperature that typically characterize composting operations. It is also significant that the bulk of the monomers resulting from degradation, i.e. the acids and the glycols, are readily digested by organisms in solid waste or compost to create carbon dioxide, methane and water.

Preferred polyesters are herein indicated by abbreviations, such as 2G/DEG-T/5SI/5 and/or 6, containing up to 20 mole % of DEG, and containing 1.5 to 2 mole % of 5SI and 10 to 40 mole % of adipic and/or glutaric acid. As in the aforesaid applications, numbers are used to connote the mole percentages of the glycol (other than 2G) and of the diacid monomeric units (other than T) in the polyester, while any PEG content may be denoted in weight (w) % of the total polymer, if so indicated, or by numbers like the other mole percentages if not so indicated.

The blends provide useful materials having applications in end uses where containment of body fluids is necessary and disposability is desirable, e.g., in a degradable film or in a fabric or paper coated with a film which will conform easily to body contours yet act as an effective barrier to penetration of body fluids. It is especially preferred that such a film or coated sheet should have a reduced tendency to rattle and rustle when flexed during body movements. Such a film or coated sheet must have adequate strength and toughness to allow its survival during use. In order that it not leave objectionable residues when disposed of, it should disintegrate quickly when placed in proper waste disposal facilities and, ultimately, degrade substantially completely to innocuous materials, such as carbon dioxide, methane and water.

Many copolyesters which are copolymerized with 5-sulfoisophthalic acid (5SI) will hydrolyze readily. Not all such copolymers are acceptable in the end uses contemplated. The polymers should exhibit the desired physical properties, and be processable under practical conditions, but the products of hydrolysis should desirably have the potential to be digested by the organisms likely to be found in waste disposal facilities and compost. This cannot be achieved by all monomers used in preparing other copolyesters. We have found, for example, that terephthalic acid is decomposed substantially completely in such a test over 28 days, and that ethylene glycol and polyethylene glycol with MW 250 and 3500 are also satisfactorily digested by organisms typical of those found in waste disposal systems; typically, as the molecular weight increases, degradation generally becomes slower. Non-aromatic acids (such as adipic acid and glutaric acid) are known to be decomposed rapidly, and hydrolysis of carbonic acid gives carbon dioxide and water directly. Sodium dimethyl 5-sulfoisophthalate, which has shown slower degradation in these tests, constitutes only a very small proportion of the copolymers. In this regard, it should be recognised that the rate and extent of decomposition is affected significantly by selection of particular organisms and other specifics during composting.

As indicated, if desired, hydroxy acid residues may be incorporated. This may be effected by transesterification carefully to provide copolyesters containing, by weight of the copolyester, at least about 60% of glycol/diacid polyester as discussed and illustrated in first part of Formula (I) with up to about 40% consisting essentially of structural units of the formula [—C(O)—Q—O—], and wherein Q is such that the hydroxy acid HO—C(O)—Q—OH, which may be a polyhydroxy acid, has a melting point at least 5° C. below its decomposition temperature, and Q is preferably —$CH_2$—, —$CH_2$—$CH_2$—, —$CH_2$—$CH_2$—$CH_2$—, —$(CH_2)_5$—, —$C(CH_3)H$—, or —$C(R')H$—$CH_2$—, where R' is selected from the group of —$CH_3$ and —$CH_2$—$CH_3$, similar to the copolyesters more fully described in aforesaid application Ser. No. 07/645,995.

MORE DETAILED DESCRIPTION OF PREFERRED EMBODIMENTS

The polyesters of the blends herein consist essentially of recurring structural units of the formulae

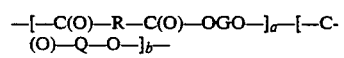

wherein up to about 40 mole % of R is selected from the group consisting of a chemical bond and one or more divalent, non-aromatic, $C_1$-$C_{10}$ hydrocarbylene radicals, and the remainder of R is at least about 85 mole % p-phenylene radical, wherein G is up to about 30 mole % of a polyethylene ether radical selected from the group consisting of

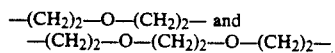

and the remainder of G is selected from the group consisting of polyalkylene ether radicals of molecular weight at least about 250, and —$(CH_2)_2$—, —$(CH_2)_3$—, and —$(CH_2)_4$— radicals, wherein Q is derived from an hydroxy acid of formula

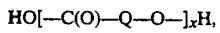

where x is an integer, such hydroxy acid having a melting point at least 5 C below its decomposition temperature, and Q is selected from the group consisting of a chemical bond and hydrocarbylene radicals —$(CH_2)_n$—, where n is an integer from 1 to 5, —$C(R')H$—, and —$C(R')HCH_2$—, wherein R' is selected from the group of —$CH_3$ and —$CH_2CH_3$, and wherein "a" and "b" are mole fractions of the polymer, and the mole fraction "a" may be 0.6 to 1 and, correspondingly, mole fraction "b" may be 0 to 0.4, and wherein about 0.1 to about 15 mole %, preferably about 0.1 to about 2.5 mole % of the polymer contains alkali metal or alkaline earth metal sulfo groups, especially about 1.5 to about 2 mole % of such groups.

If desired, some of the G may be a radical of a polyalkylene glycol of (number average) molecular weight (MW) at least about 250, as disclosed in our copending application Ser. No. 07/645,849, e.g. polyethylene glycol (PEG).

Thus, of the R radicals, up to about 40 mole % may be an alkylene or other residue from an organic $C_2$-$C_{12}$ non aromatic dibasic acid, with at least about 85 mole % of the remainder, (about 60 to 95 mole %) being T (para-phenylene), with optional inclusion of up to about 15 mole % of I (meta-phenylene).

Of the G radicals, about 1 to 30 mole % are preferably DEG and/or TEG (i.e., polyethylene ether radicals —$(CH_2)_2$—O—$(CH_2)_2$— and —$(CH_2)_2$—O—$(CH_2)_2$—, respectively). Optionally, if desired, some may be PEG (a radical of a polyalkylene glycol of MW at least about 250), with the remainder being 2G, 3G and/or 4G (i.e. $C_2$-$C_4$ lower alkylene groups).

Any Q radicals are from an hydroxy acid, as indicated above.

Importantly, the polymer contains sulfo groups, such as are described in U.S. Pat. No. 3,018,272 (Griffing and Remington), the disclosure of which is hereby incorporated by reference. The amount of sulfo groups in the polymer should be up to 15 mole %. Thus, up to 15 mole % of the R may be 5SI and/or 4SP radicals, as described herein, or may be another sulfo group suggested by Griffing et al. Or, if desired, up to 15 mole % of the G may be the sulfo group. Thus the content of sulfo group-containing radical is calculated with respect to the recurring structural units of the formula [—C(O)—R—C(O)—OGO—]. Such radicals may, however, be contained in other units, i.e., other than in the R or G units, for instance in end groups, if desired. The radicals containing sulfo groups need not necessarily be aromatic, although 5SI and 4SP have given good results. Preferred amounts are about 0.1 to 2.5 mole %, especially 1.5 to 2 mole %. Such preferred polyesters are not soluble in water, although such polyesters derivable from the same constituents, but with higher mole percentages of 5SI, maybe useful in certain blends for special purposes. They also have relatively low glass transition temperatures, Tg.

Thus, advantageously the Tg of the polyester fibers or films should be no higher than approximately the temperature at which degradation will take place. Since the temperatures in composting operations are often no higher than about 70° C., it is desired that the Tg of the polyester be no more than about 70° C., preferably about 65° C. or below. Commercial unmodified polyethylene terephthalate (abbreviation 2GT) polyester fibers have a Tg of about 80° C. Even a 2G-T polyester containing 2.5 mole % of 5SI has a Tg value of 76° C. The replacement of some terephthalic acid with an aliphatic acid, such as azelaic, succinic, adipic, sebacic or glutaric acid, is advantageous in lowering the Tg.

The organic non-aromatic dibasic acid is preferably adipic and/or glutaric acid, but may be azelaic, succinic, sebacic or other acid, ranging from oxalic acid ($C_2$) to dodecanoic acid ($C_{12}$), as dibasic acids having larger numbers of carbon atoms are not yet commercially available. The aforesaid parent applications provide for incorporating small amounts of such aliphatic acids. The more of such acid that is added, the more significant is the effect of such incorporation. It is not, however, desirable to lower the melting point of the polymer to such an extent as to impair its usefulness, depending on the desired end-use, and is generally desirable to incorporate no more than about 40 mole % of such acid. Preferred amounts are 10–30 mole %.

It will be understood that, with minor variations in composition, it is possible for the polyesters to have a further significant reduction in their Tg values. For example, the replacement of up to 5 mole % of the ethylene glycol with a polyethylene ether glycol, such as DEG or TEG (triethylene glycol), can also lower the Tg. Such amounts will not otherwise materially alter the degradation characteristics of the polyesters, hence their inclusion is contemplated by the term "consisting essentially" used to describe the polyesters used in the blends and other products of the invention.

Minor amounts of polyfunctional branching agents, such as trimellitic acid residues, may be incorporated to modify melt rheology and film processing, if desired.

The glycol component may advantageously contain a polyethylene ether radical, such as DEG or TEG, to achieve an optimum level of degradability without a major sacrifice to fiber and film physical properties such as tensile strength. Above about 40 mole % DEG such properties are adversely affected, as indicated by Tietz.

The acid component preferably includes about 1.5 to 2 mole % 5SI. This component is not only relatively costly but also excessively large amounts can render the polyesters water soluble and thus affect the fiber and film physical properties such as shrinkage. As little as 0.1 mole % of 5SI contributes significantly to the degradability characteristics of the resultant fibers and films. Alternatively, as indicated, other sulfo group-containing units may be included, as taught in U.S. Pat. No. 3,018,272. In such monomeric units, the metal ion is preferably an alkali metal such as sodium, potassium or lithium. However, alkaline earth metals such as magnesium are also useful. A 5-sulfoisophthalate that has given very good results is the sodium salt.

A relative viscosity of at least 16, preferably at least about 18, is generally acceptable for melt spinning performance.

The polyesters may be prepared by conventional polycondensation techniques using, for example, as the glycol component, a combination of about 15 to 20% by weight of the polyalkylene ether glycol, with a complemental molecular amount of ethylene glycol, and, as the acid component, a combination of about 10 to 40 mole % of the non-aromatic acid, about 45 to 89.9 mole % of terephthalic acid and about 0.1 to 15 mole % of a metal salt of 5-sulfoisophthalic acid, which is a preferred component containing the sulfo groups. Any carbonic acid residues are conveniently introduced by transesterification. Optionally part of the ethylene glycol can be replaced by another glycol, as indicated. In lieu of the mentioned dicarboxylic acids, ester-forming derivatives such as the dimethyl esters of the acids may be used.

In the Examples herein, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage, followed by addition of the remaining components, which may be polymeric such as polyethylene adipate, polylactide, polyglycolide or polycaprolactone [6E], and completion of the polymerization.

The sulfonate-containing polyesters are very hydrolytically sensitive, having a higher equilibrium moisture content than 2G-T resin and a faster moisture regain rate. This is particularly important for blending with starch. It is desirable that isolated flake be dried thoroughly, preferably to a moisture content below 200 ppm before reextrusion, and to maintain a nitrogen atmosphere around all possible air in leakage points, and to transfer polymer in warm condition (e.g., above about 50° C.) from the dryer to the extruder.

The polyesters as isolated from the reactor usually have multiple melting points by DSC analysis. These are seen at temperatures which overlap those which might be used in drying 2G-T flake, making it difficult to dry these polymers without fusing the flake into a solid mass when they are rapidly heated to get fast economical drying rates. Slower heating to allow crystallization, after which heating at higher temperatures for fast drying, is desirable.

A desirable procedure for preparing high molecular weight resins from rapidly polymerized lower molecular weight ones may be to use solid phase polymerization of low molecular weight flake. This procedure may desirably be carried out after or in combination with the crystallization procedure mentioned above so that temperatures high enough for rapid polymerization can be attained without fusing of the flaked resin. In addition, as known from U.S. Pat. No. 3,544,523, anticaking agents may be useful to prevent sticking, such as Cab-o-sil grade MS-75D, or other finely divided inert solids, like $TiO_2$, talc, carbon black and clay. The starch itself has also been found to be useful for this purpose.

If it is desired, for environmental or other reasons, to avoid use of a catalyst that comprises antimony or another heavy metal, then this may be achieved, for instance, by using a crystalline sodium aluminosilicate molecular sieve such as Linde Molecular Sieve 13X, type 9356, with a nominal pore size of 10A, obtained from Union Carbide Corporation. Such procedure is more fully described by Jackson in U.S. Pat. No. 5,041,525, issued Aug. 20, 1991, but other methods of avoiding antimony may be used, if desired.

In any event, the particular mole percentages of the aforementioned components are desirably selected to provide a polyester which in fiber or film form has a Tg of 70° C. or less, preferably of about 65° C. or less.

As will be understood, while the blends of the invention are well suited for use as fibers or filaments in nonwoven sheets, they can be used to particular advantage in the form of cast and blown films, foams, coatings, laminates, molded articles, or wherever blended polyesters with such properties are desired.

Fibers and filaments herein are interchangeable terms in the general sense, but where a more specific acknowledgement of length is appropriate, the term "fibers" is intended to refer to short filaments as in "staple fibers". Hereafter only one of the terms may be used.

In order to blend starch with the polyesters according to the invention, stringent precautions (beyond those which one might normally expect to be necessary for processing more conventional polyesters) must be taken to avoid molecular weight reduction of the polyesters via hydrolysis. Thus reextrusion of 2G-T pellets can normally be effected if the moisture content is controlled to a value of about 200 ppm or less. The polyesters that are blended with starch according to this invention are intrinsically very sensitive to hydrolytic degradation, especially at high temperatures such as are generally necessary for processing the blends. It is preferred, therefore, that the moisture content of the polyester be maintained no more than about 50 ppm, during hot processing. The starch should also be dried, but only needs drying to a moisture level less than about 1%. Starch is known to contain both bound and free water so such an apparently high water content (higher than that for the polyester) may not be so deleterious as one might have been expected, from the comments above, relating to the more sensitive polyesters—especially if the polyester water content has been reduced to the indicated level. The desired levels of moisture can be attained by drying both starch and polymer at 80 C. for 16 hrs under a vacuum of 25 in. of water under a purge of dry nitrogen. In order to prevent moisture uptake of the materials, they should desirably be dried in preparation for blending, and then maintained and transferred in a warm state (above 50 C.) under a dry (−40 F. dew point) air or nitrogen atmosphere.

Also, when the polyester/starch blends are formed into pellets for reprocessing into shaped articles such as film, fiber, foam, etc., stringent precautions should be taken to prevent moisture uptake from the atmosphere. After redrying under the conditions specified for the polyester and starch, the pellets should be transferred in a warm (above 50 C.) state to the processing site (e.g. the inlet of an extruder) and maintained under a dry atmosphere.

Because of this greater sensitivity to molecular weight reduction by moisture, it is preferred that all the processing, from making a blend through to shaping the articles be carried out with as few steps as possible. Thus, combining the dried starch with dry polyester and additives in an extruder and forming the extrudate directly into the desired final article, such as a film, foam or fiber in a simple continuous operation, or as a coupled process, is generally much preferred, from an ease of processing standpoint over intermediate formation of reextrudable pellets, that need reprocessing with the above precautions to avoid degradation by moisture.

The blends of the invention may be converted to fibers or filaments by melt spinning techniques, that take into account the precautions mentioned above to avoid moisture. Deniers of 2 to 15 dpf are most common. The filaments may be used as-spun (undrawn) or in a stretched (drawn or oriented) condition. Drawing to reduce denier or for increasing orientation can be accomplished by the usual procedures.

The compositions of the invention can be formed into nonwoven fabrics via a number of processes. These may be roughly divided into spunbonded fabrics and those fabrics using staple fibers. These are discussed in "Encyclopedia of Textiles, Fibers and Nonwoven Fabrics", Ed. Martin Grayson, John Wiley and Sons, New York, 1984, pp 252-304. The compositions described herein can be used in many such products. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to strong fabrics with tensile properties which are usually superior to those obtained with staple webs. Bonding can also be carried out by using suitable adhesives and both these methods may be used to make point bonded or area bonded fabrics. Needle punching may also be used to give the webs stability and strength. Spunbonded fabrics can also be made by melt blowing from these blends, provided the drying and handling conditions outlined above are followed. In this process, a stream of the molten blend is extruded into a high velocity stream of heated dry air and a bonded web formed directly on a screen conveyor from the resultant fibers. Nonwoven fabrics can also be made by direct extrusion through a rotating die into a netlike product (U.S. Pat. No. 3,959,057 J. J. Smith) or by stretching and drawing embossed films of the thermoplastic polymers (British Patent 914,489 and 1,548,865 to Smith and Nephew Research Ltd.).

Staple fibers can be made into nonwovens by several processes. Most of these can be classified into (1) web preparation and (2) reinforcing ("Manual of Nonwovens", Dr. Radko Krcma, Textile Trade Press, Manchester, England, pp 74-76, 1971). During web preparation, bales of staple fiber are opened and formed into a web having either a random orientation (via air, or electrostatic deposition) or parallel or crosslaid orientation (via carding and plying). Reinforcement to impart physical integrity and useful mechanical properties can be accomplished by mechanical means such as needlepunching or hydroentanglement (where water jets move fibers out of the plane of the web and entangle them) as in the spunlaced fabrics (U.S. Pat. No. 3,485,706 to Du Pont) or by stitchbonding where a reinforcing thread is sewn through the web. (See "Principles of Stitch Through Technology" Nonwovens Fabrics Forum, Clemson University, Clemson, S C 1978 by J. D. Singelyn). Dry adhesive powders may also be applied to the staple web prior to a heating step to produce a powderbonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e. cotton and rayon.

In addition, useful articles can also be made by laminating, extrusion melt coating or adhesively combining the above types of nonwoven fabrics with each other, with films or with staple webs in such a way as to confer desired properties on the combined fabric.

In particular, a fabric made by extrusion melt coating a thin, pinhole free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable fibers described herein may be used in all these methods of preparing nonwovens to yield fabrics which when subjected to composting conditions will be substantially degraded. Thus staple webs of the fibers, as well as blends of these fibers with cotton and rayon, may be bonded by hydro-entanglement, by needle punching, and by dry adhesive bonding. (The adhesives used should be chosen to allow the desired degradation under composting conditions.)

Thermally bonded staple webs of the compostable fibers can be made in the 100% form or webs containing a significant proportion of these fibers together with cotton and/or rayon may be thermally bonded to fabrics having useful mechanical properties.

Continuous or spun yarns prepared from the compositions described herein may be used to stitch bond webs of fibers such as cotton, rayon or blends of these fibers, or wood pulp, with the compostable fibers of this invention resulting in fabrics which will degrade under composting conditions.

Spunbonded fabrics can be made by thermally bonding webs of continuous fibers prepared from the compostable polyester compositions described herein, and by blow spinning, direct extrusion to nets and drawing of embossed films.

The compostable compositions described herein can be melt extruded as films to coat spunlaced nonwoven fabrics which themselves may be composed of compostable fibers alone or in combination with wood pulp, rayon or cotton.

A process for preparing ultramicrocellular and plexifilamentary products is disclosed in U.S. Pat. No. 3,227,784 (Blades et al) and durable plexifilamentary and microcellular products are described in U.S. Pat. No. 3,227,664 (Blades et al) and U.S. Pat. No. 3,081,519 (Blades et al).

Extrusion of foamed plastics has also been described, for example in Modern Plastics Encyclopedia Oct. 1990 Vol 67 #11 pp 291-2. In foam extrusion, molten polymer is first mixed with a relatively small amount (e.g. 1 to 15 wgt %) of a blowing agent. The blowing agent used does not have to be a true solvent for the polymer. When the mixture is extruded, the blowing agents expand due to depressurization and/or volatilization to form a microcellular structure. Unlike in flash spinning, most of the blowing agents used do not leave but stay inside the foam. Most commonly used blowing agents are: 1). gaseous materials such as nitrogen and carbon dioxide, 2). low boiling organic solvents such as hydrofluorocarbons (e.g. HFC-134a, 152a, 125), hydrochlorofluorocarbons (e.g. HCFC-22, 123, 141b, 142b, 124), and hydrocarbons (e.g. isobutane, pentane). In addition to these types of physical blowing agents, chemical blowing agents are also used to make foams. Chemical blowing agents decompose at elevated temperatures or through chemical reaction to generate gases. Nucleating agents which are finely divided powders such as fumed silica are usually added to encourage the formation of small uniform cells.

Nonwoven webs of the compostable compositions made by the melt blowing process may also be used as an adhesive layer between other nonwoven fabrics.

It is apparent that the fiber, film, foam, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of and degraded in composting systems. The following is a nonexclusive list of such end uses:

Agricultural mulch
Agricultural mats containing seeds
Nutrients
Adhesive tape substrate
Baby pants
Bags
Bag closures
Bed sheets
Bottles
Cartons
Disposable diapers
Dust bags
Fabric softener sheets
Garment bags
Garbage and lawn waste bags
Industrial bags
Labels, tags
Monofilaments
Packaging materials and structures
Pillow cases
Protective clothing
Surgical drapes
Surgical gowns
Surgical sheets
Surgical sponges
Tampon applicators
Temporary enclosures
Temporary siding
Toys
Wipes.

The invention can provide fluid impermeable sheets which are compostable in typical waste disposal facilities. Preferably these sheets should not rattle or rustle objectionably and should have strength and toughness adequate for use in personal absorbent products, such as disposable diapers.

The fibers, films, foams and nonwoven fabrics prepared from the blends of the present invention are of particular utility in disposable diapers since in that use they have an enhanced capability of being degraded in a composting operation. Typical examples of disposable diaper constructions are given in U.S. Pat. Nos. 3,860,003 (Buell) and 4,687,477 (Suzuki et al.), the disclosures of which are incorporated herein by reference. Items which can be made of the compostable compositions of this invention include:

(1) the backsheet film, i.e., the water-impermeable outside layer, which may be a film which is 100% of the compostable composition or it may be a laminated sheet with a nonwoven or web of compostable fibers including cotton or rayon adhered to the film, or it may be a film adhered to a suitable grade of paper, (2) the topsheet, i.e., the water permeable or inner layer, which is a film of a composition of the invention or nonwoven fabric of the compostable fiber composition or a blend of the compostable fiber of this invention with cotton or rayon fiber, having a porosity suitable for passing urine quickly to the fluid absorbing pad between the topsheet and backsheet, (3) the fastening tapes which may optionally be made from films or nonwovens of the compositions of the invention; the fastening tapes are typically coated with a pressure sensitive adhesive, (4) the frontal landing strip, which may be made from films of this invention; the frontal landing strip is typically printed with a decorative design and coated with a pressure sensitive adhesive, (5) the flexible foam optionally inserted into the diaper under modest extension to gather the waist, leg openings, and/or barrier leg cuffs may be made from polymers of this invention, (6) hot melt adhesives used to bond the diaper components to one another may be formulated to incorporate polymers of this invention, (7) the leakage shield used at the diaper waist, in front and back, may be made from films of this invention, and may be glued, thermally bonded, or sonically bonded to the topsheet or the topsheet and backsheet, (8) additives to the absorbent cellulose pulp core, which may be short fibers, fibrids, synthetic pulp prepared by flash spinning, or some other mechanically dispersable and finely divided form made from polymers or fibers of this invention, and which serve to increase wet strength of the core, particularly when superabsorbent polymers have been incorporated and pulp content subsequently reduced, (9) other minor components of the diaper which require the combination of compostability and thermoplastic fabrication and/or processing, and

(10) diaper packaging, which may comprise a bag made of film of compositions of this invention, or paper or cardboard coated with film and/or reinforced with fibers of compositions of this invention.

It will be apparent that the products of the invention may contain additives such as dyes, fillers, pigments, plasticizers, etc. Indeed, use of appropriate fillers or other additives may be helpful, as an acceptable way to enhance disintegratability. The incorporation of finely divided particulates has been found helpful, for instance incorporating calcium carbonate in similar compositions. As the incorporation of large amounts of such a filler may increase the tendency of articles to embrittle to an extent that could be undesirable for certain end uses, it may be desirable to take steps such as adding a plasticizer to counter such tendency. Indeed, the addition of materials such as low molecular weight polyethylene adipate (Rucoflex $Mn=2000$) to particulate blends has been found to provide further advantage in accelerating disintegration under composting conditions. Also, in regard to such filled articles, microporous films are taught by Moss in U.S. Pat. No. 4,698,372, and similar techniques may be followed with products of the present invention. Advantageous results have also been obtained by using blends of related compositions with tartarates and citrates, such as dibutyl tartarate and triethyl citrate. The addition of low molecular weight polyethylene adipate (Rucoflex Mn=2000) has also been shown to reduce rattle or rustle of the films of this invention. So incorporation of appropriate additives would be expected to be advantageous for the blends of the present invention.

TEST METHODS

Polyester glass transition temperatures, Tg, are obtained by using a Du Pont model 2910 Differential Scanning Calorimeter. Samples are heated under a nitrogen atmosphere at a rate of 20° C./min. to a temperature 10°–20° C. above the melting point, then the melt is cooled using the rapid air quench capability of the instrument. The Tg is determined from the second cycle scan done at 20° C./min. using the internal software to determine the inflection point of the baseline shift.

Polymer melting point, m.p., is determined on the first heating cycle as described in Tg determination. The temperature at which the highest endothermic peak occurs is reported as the polymer melting point.

Number average molecular weight, Mn, is determined by gel permeation chromatography (gpc) versus a standard polyethylene terephthalate sample with an Mn of 22000 and a weight average molecular weight of 44000. Polymers are dissolved in and the analysis is run using HFIP (hexafluoroisopropanol) containing 0.01M sodium trifluoroacetate as the solvent. A Waters model 150C ALC/GPC instrument, or its equivalent, is used with two Zorbax PSM-S biomodal columns (sold by E.I. du Pont de Nemours and Company) (or equivalent) in series at 30° C. A refractive index detector was used and data collected at 100 intervals and analyzed via software provided by the instrument supplier.

Carboxyl end groups are determined by titration of an o-cresol solution of the polymer at 115° C. with KOH in benzyl alcohol to a colorimetric endpoint using bromophenol blue as the indicator. Results are reported in eq./$10^6$ grams of polymer.

Inherent viscosity is defined in "Preparative Methods of Polymer Chemistry", W. R. Sorenson and T. W. Campbell, 1961, p. 35. It is determined at a concentration of 0.5 g/100 ml of the indicated solvent at the indicated temperature, usually HFIP at 30° C.

Relative viscosity is the ratio of the viscosity of a solution of 0.8 gram of polyester dissolved in 10 ml of hexafluoroisopropanol (HFIP) containing 80 ppm $H_2SO_4$ to the viscosity of $H_2SO_4$-containing HFIP itself, both measured at 25° C. in a capillary viscometer and expressed in the same units.

Crimp index is measured by straightening a crimped tow by application of about 0.1 gpd load. Then 0.5 gm clips 66.6 cm apart are attached to the extended tow. The tow is then cut 11.2 cm beyond each clip to give a sample of 90 cm extended length. The sample is suspended vertically, hanging freely from one of the clips to allow retraction to crimped length. After about 30 secs., clip to clip distance is measured.

$$\text{Crimp Index} = \frac{(66.6 - Lc)}{66.6} \times 100$$

where Lc is the clip-to-clip distance in the free-hanging state.

Crystallinity index is measured by first obtaining a diffractogram as described by Blades (U.S. Pat. No. 3,869,429, col. 12) with some modifications. The high intensity X-ray source is a Phillips XRG-3100 with a long fine focus copper tube. Diffraction is analyzed with a Phillips single axis goniometer equipped with a thetacompensating slit and a quartz monochromator set to exclude copper $K_b$ radiation. Diffracted radiation is collected in step scanning mode in 0.025 steps with a 1.5 sec. per step count time. The digital data so collected are analyzed by a computer and smoothed by a running fit to second order polynomial. The computer is programmed to define a straight base line which joins the diffractogram tangentially at about 113 and 343. Crystallinity index is defined as $$\frac{A \times 100}{A - B}$$

where A is the intensity of the 18° 010 peak above this base line and B is the intensity of the 20° minimum above this base line. Crystallinity index has been related to percent crystallinity determined by density (see U.S. Pat. No. 4,704,329, col. 8,9). Weight percent crystallinity=0.676 X Crystallinity index.

Tensile Properties of fibers and yarns are coded as T/E/M/To for tenacity, elongation, initial modulus, and toughness and are reported in their conventional units of grams per denier, percent, grams per denier, and grams per denier. These are measured on conditioned (65% RH, 70 F) samples (3 inch gauge length) in a commercial testing machine at the rate of extension of 50% per minute (unless otherwise indicated). Toughness (To) is measured as the integrated area under the stress-strain curve. Any counterpart properties of fabrics are similarly coded as T/E/M/To and are reported in units of lb./in./oz./sq.yd., percent, lb./in./oz./sq.yd., and lb./in./oz./sq.yd., respectively. Fabric samples are 1 inch X 8 inches (with 5 inches gauge length), are conditioned prior to testing, and are extended in a commercial testing machine at a rate of 100% per minute. Paper laminates are tested as 1 inch wide strips at a 5 inch gauge length at 100% E/min after conditioning at 65% RH 70 F. Results are reported as T/Emax/Eult/M/To (Tenacity at maximum load/Elongation at that load/Ultimate elongation at break/Initial Modulus/Toughness). The corresponding units are lb/in/oz/yd$^2$/%/%/lb/in/oz/yd$^2$/lb/in/oz/yd$^2$.

For films, these are coded as T/E/M/To for Tenacity, Elongation, Initial Modulus, and Toughness, and are reported in units of ksi/percent/ksi/ksi. Film samples used in the testing were approximately ⅛ inch wide. Testing was done on a commercial testing machine, 1 inch or 2 inches gauge length, depending on sample available, at 100% elongation/minute. All testing was at 70 F and 65 RH.

The invention is further illustrated by the following Examples; polymer composition are generally given as mole %, it being understood, however, that some deviation in composition may result from generation of DEG as a by-product during polymerization and its incorporation in the copolymer in minor amounts; other parts and percentages are by weight, unless otherwise indicated.

EXAMPLE 1

This shows that starch can be blended with a 5SI containing polyester to give a well-dispersed blend which yields useful film, and an evaluates the films ability to degrade in a composting facility in comparison with a similar film without starch, as a control.

COPOLYESTER RESIN PREPARATION

The copolyester resin was made to the following composition:

R=
- 58.1 mole % T (from Terephthalic acid)
- 39.9 mole % 5 (from glutaric acid)
- 2 mole % 5SI G=
- 89.7 mole % 2G
- 10.3 mole % DEG In a 35 gallon reactor containing a stirrer, a nitrogen inlet and a distillation column were placed:
- 27215 grams Dimethyl Terephthalate
- 28757 grams Ethylene Glycol
- 15422 grams Dimethyl Glutarate
- 2630 grams Diethylene Glycol
- 1452 grams 5SI Dimethyl Ester
- 29 grams $Mn(OAc)_2 \cdot 4H_2O$
- 9.1 grams $Na(OAc) \cdot 3H_2O$
- 41 grams $Sb_2O_3$ The temperature of the reactor was slowly increased. Distillate (methanol) was collected in excess of the amount of 15,000 ml between 160° C. and 211° C. A second distillate (ethylene glycol) in the amount of 5800 ml was collected between 211° C. and 240° C. The resulting oligomer was transferred to a second vessel containing an agitator and vacuum capabilities. Then 20 grams of 85% phosphoric acid were added to the transferred material, the temperature raised to 275° C. and the maximum vacuum (0.9 mm Hg) was established over 90 minutes. After 1 hour and 50 minutes at these conditions, the contents of the reactor were discharged through a strand die into water quench and then cut into pellets.

Starch (Cream* Pure Corn Starch Lot-L120Z2 from The Dial Corporation, Phoenix, Az) was dried at 90° C. overnight in a vacuum oven using house vacuum and a slight nitrogen purge. The polymer pellets were dried at 70° C. overnight in a vacuum oven using house vacuum. The blends were made in a mixing chamber (Haake Buchler Rheomix 600 with high shear stainless steel roller roters) driven by a C. W. Brabender drive unit with a PLD-651 data processor. The nominal free volume of the mixer was 72 cc with a goal working volume of 61 cc. The temperature of the chamber was set at 130° C. and the rotor started turning at 25 RPM. 55 g of 75 wt % polymer and 25 wt % starch were rapidly preblended while still warm, placed in the mixing chamber and mixed according to the following program:

TABLE 1

| Time (seconds) | Setting (RPM's) |
|---|---|
| 0-55 | hold 25 |
| 55-60 | ramp to 74 |
| 60-295 | hold 74 |
| 295-300 | ramp to 75 |
| 300-600 | hold 75 |

Blending was terminated when temperature and torque levels out. The final blend temperature was 150° C. after about 10 min. The sample was removed, quenched in liquid nitrogen and shattered to smaller pieces.

The blend mixture containing 25 wt % starch was dried in a vacuum oven at 45° C. and pressed in a press with heated platens (Pasadena Hydraulics Inc. City of Industry Ca. Model SPWR228C-X1-3-5-3) between sheets of polytetrafluoroethylene to minimize sticking. The press temperature was 125° C., and the load applied was 10,000 lbs for 3 min. The resulting film was clear (printing being read through it easily surprisingly, only slightly more haze was present than in a control film containing no starch), limp and 5-10 mils thick. Inspection under a microscope at 340X showed welldispersed starch granules. This film and a control film without added starch were marked for identification by bolting together polytetrafluoroethylene washers on each side of the sample, and were placed in a rotary composter with 2/1 municipal solid waste/sewage for 28 days, as described in Example 6 of copending application Ser. No. 07/834,794.

The starch-containing film was completely eroded and disintegrated in the area exposed to the compost.

Much of the control film (without starch) was eroded in the exposed area also but there were some shreds still attached to the polytetrafluoroethylene sample holder. Molecular weight (Mn) determinations were made by gpc and showed only some 54% loss, from an initial value of 40920 to 18980 (each of these values being an average of 2 determinations).

Blends with 25% corn starch can be made by similar methods using copolyesters of the following compositions:

2G/DEG(60/40)-T/5SI(98/2)

2G/DEG/PEG(Mw=600)(86.5/6.5/7)-T/5SI(98/2)

[2G/PEG(Mw=600)(94/6)-T/5SI(97.9/2.1)]//-[6E](86//14 Wt %)

EXAMPLE 2

This compares the properties of three blends of polymers with starch. Polymer A was a copolyester containing 5SI. Polymers B and C do not contain 5SI.

COPOLYESTER RESIN PREPARATION

The polymers were made to the following compositions:

| Polymer MP (C) | A 170 | B 160-165 | C 202 |
|---|---|---|---|
| | 78% T | 80% T | 80% T |
| | 20% 5 | 20% 5 | 20% 5 |
| | 2% 5SI | 70% 2G | 90% 2G |
| | 90% 2G | 30% DEG | 10% DEG |
| | 10% DEG | | |

Polymers A and C were made by procedures like those in Example 1, using similar ingredients except for the inclusion of 5SI in Polymer A.

Polymer B was made as described below, with additional DEG included in the Polymer B charge to lower the polymer melting point close to that of Polymer A.

In a 1000 cc 4 necked resin kettle fitted with a mechanical stirrer, condenser, distillation head with receiver flask, and a capillary $N_2$ inlet tube were placed:
158.1 g ethylene glycol 47.7 g diethylene glycol (DEG)
0.230 g Mn(OAc)$_2$.4H$_2$O
0.286 g Sb$_2$O$_3$ This was warmed to 160° C. to bring the contents of the flask into solution and 233 g Dimethyl terephthalate (T)
48 g Dimethyl glutarate (5)

were added and the temperature gradually raised to 220° C. while methanol distillate was collected. Then 0.5 ml of a H$_3$PO$_4$ solution (4.79 g of 85% H$_3$PO$_4$ diluted to 50 ml with ethylene glycol) was added. The resultant molten monomer was poured into 2 polymer tubes to fill them about ⅔. A capillary inlet tube drawn to a fine point was inserted to reach to the bottom of the tube and a filter flask attached to the sidearm of the tube to act as a receiver. Polymerization was continued by heating the tube in a dimethyl phthalate vapor bath (284° C.) first under laboratory vacuum for about 1 hour, and then at about 0.4 mm Hg over 2.5 hours. The capillary was removed from the molten polymer and after cooling the polymer was recovered from the tube and ground into small particles in a Thomas mill.

BLEND AND FILM PREPARATION

Blends of 25 wt % starch were made with Polymers A, B and C in the apparatus and using the procedure in Example 1.

The starch blends with the Polymers A, B, and C were pressed into films using the procedure in Example 1. A temperature of 175°–180° C. is used for Polymers A and B and 205° C. for Polymer C. The Polymer C/starch blend film was brittle. The film properties are shown in Table 2A.

TABLE 2A

| Composition Wt % | Film Thick (mil) | Film Appearance | T/E/M/To ksi/%/ksi/ksi |
|---|---|---|---|
| 75% A/25% starch | 3.5 | sl. hazy | 2.9/3.2/170/.07 |
| 75% B/25% starch | 1.7 | " | 5.8/71/148/0.8 |
| 75% C/25% starch | 2.5 | hazy | 3.4/1.4/259/.018 |

Strips of these films about ⅜ inches wide were drawn 4.5× over a 55° C. heated pin for A and B, and 3.4× at 65° C. for C, to yield the following machine direction (MD) properties:

TABLE 2B

| | | Tensile | |
|---|---|---|---|
| 75% A/25% starch | 1.8 | white, opaque | 11.6/57/208/1.8 |
| 75% B/25% starch | 1.4 | " | 4.2/85/84/0.74 |
| 75% C/25% starch | 1.2 | " | 3.8/14/121/0.13 |

The much lower modulus values obtained for the films from blends with Polymers B and C is believed to indicate that debonding has taken place between the starch particles and the polymer phase, probably during drawing of such films, whereas little or no such effect occurred with the blend from Polymer A.

Hydrolysis

Pieces of the undrawn Polymer/starch films, about 2 cm×2 cm in size, were placed in 200 ml of deionized water contained in a capped Erlenmeyer flask and shaken in an air thermostat at 60° C. for 8 days. The Polymer A/starch film embrittled and broke into fragments during this treatment while the Polymer B and C films remained intact.

The molecular weights (Mn) of the polyester films before and after treatment are in the following table:

TABLE 2C

| | Mn | |
|---|---|---|
| | Initial | 60 C., Water 8 Days |
| 75% A/25% corn starch | 29740 | 8710 |
| 75% B/25% corn starch | 25480 | 26110 |
| 75% C/25% corn starch | 24240 | 21290 |

(The higher Mn values after hydrolysis with polymer B may be due to extraction of oligomers by the water)

Compost Testing

Thirty six approximately equally sized undrawn film samples, 9 from each of Polymers A and B, both with and without starch, were enclosed in polyethylene net bags having a ¼ inch mesh size and placed in a rotary composter (Kemp Compostumbler) with a mixture of municipal solid waste and municipal waste water treatment sludge, and allowed to compost for 28 days, turning every week and adding water to maintain the moisture content above 40%. The total amounts recovered for each Polymer were as follows:

Polymer A alone: 1.5 g
Polymer A/25% starch: 0.6 g
Polymer B alone: 3.4 g
Polymer B/25% starch: 2.3 g This compost testing showed that blending corn starch with these polymers aided disintegration of both compositions (with and without 5SI copolymerized). However the starch blend with the 5SI-containing composition was the most completely disintegrated and is preferred for this purpose.

EXAMPLE 3

This describes the preparation of paper laminates with polyesters containing cornstarch filler and their degradation by composting.

Commercial corn starch was dried at 70 C. in a vacuum oven and a copolymer 2G/DEG(90/10)-T/5/5SI(58/40/2), prepared by a procedure similar to that described in Example 1 herein, was dried separately under the same conditions. They were mixed in the proportions shown in the Table 3 below and blended in a Brabender Plasticorder with the starting temperatures and for the times indicated. These blends were then pressed to films between polytetrafluoroethylene sheets, using a press with heated platens (model SPWR228C-X1-3-5-3-16-20 made by Pasadena Hydraulics Inc., City of Industry, Ca.) These films were laminated onto commercially available paper towels (Viva brand with 1.2 oz/yd$^2$ basis weight, 0.006 inches thick) by pressing the two together with a polytetrafluoroethylene cover sheet to prevent sticking, at 100 C. for 10–20 sec at a load of 1000 lbs.

TABLE 3

| Polymer/Starch wt % | Temp C. Init | Temp C. End | Time min. | Thick mil | Laminate thick | B.W. oz/yd$^2$ |
|---|---|---|---|---|---|---|
| 75/25 | 147 | 153 | 6 | 5 | 8 | 6 |
| 50/50 | 147 | 155 | 6 | 4 | 9 | 4.1 |
| 25/75 | 134 | 160 | 9 | 10 | did not adhere well | |

The 75% starch blend was too stiff to flow readily enough (under these conditions) to form a good laminate.

Compostability of the 75/25 copolyester/starch paper laminate was evaluated by placing it in a rotary composter with mixed municipal/sewage sludge (as described in Example 1) for 4 weeks. The sample was tagged by bolting (1/16 inch thick×1 inch square) polytetrafluoroethylene washers on the laminate. At the end of the test period, all of the laminate which had been exposed had disintegrated.

EXAMPLE 4

Table 4 shows the effect of varying DEG and glutaric acid (5) content on tensile properties of films made from blends of polyesters with starch. The melting points of the polymers used were 150° C. for the polymer used for 4A–4D, 133° C. for the polymer used for 4E–4H, and 110° C. for the polymer used for 4I–4L. The polymers were made, blends were prepared and films were prepared and tested by procedures essentially as in Example 1, except that the indicated film strips were drawn over a hot pin by hand. Results are shown in Table 4. Samples 4A–4H were pressed at 160° C. Temperatures were not recorded for Samples 4I–4L.

TABLE 4

| Sample | Polymer Comp 2G/DEG-T/5/5SI | Blend wt % Poly/St | Process draw, T | Thick mil | T | E | M | To |
| --- | --- | --- | --- | --- | --- | --- | --- | --- |
| 4A | 95/5-73/25/2 | 75/25 | — | 5.5 | 1.6 | 705 | 42 | 5.9 |
| 4B | " | " | 4X, 60C | 3.4 | 6.1 | 154 | 59 | 1.4 |
| 4C | " | 50/50 | — | 4.5 | 1.2 | 48 | 70 | .4 |
| 4D | " | " | 3X, 60C | 3.8 | 1.0 | 80 | 19 | .3 |
| 4E | 90/10-68/30/2 | 75/25 | — | 2.8 | 1.0 | 847 | .8 | 1.3 |
| 4F | " | " | 4X, 70C | 1.6 | 1.1 | 315 | 1.4 | .3 |
| 4G | " | 50/50 | — | 3.4 | .5 | 17 | 13 | .03 |
| 4H | " | " | 2.3X, 70C | 2.5 | .6 | 100 | 2 | .1 |
| 4I | 90/10-58/40/2 | 75/25 | — | 4.4 | .9 | 708 | 5 | 4.6 |
| 4J | " | " | 1.8X, 40C | 3.8 | 1.1 | 429 | 3 | 2.6 |
| 4K | " | 50/50 | — | 3.2 | .8 | 17 | 17 | .08 |
| 4L | " | " | 2X, 40C | 2.3 | .6 | 136 | 2.3 | .3 |

After samples of the undrawn films were subjected to composting for 4 weeks as described in Example 1, films from 4C, 4G, 4I and 4K were completely eroded, while 4E was 85% eroded, and 4A was embrittled, without being substantially eroded.

EXAMPLE 5

This describes the extrusion of strands of starch-/copolyester blends and evaluation of their performance in a composter. The same blends used to make the films described in Example 3 were extruded through a 0.009 inch diameter X 0.027 inch long hole at a delivery pump rate of 0.07 cc/min, to make strands that were wound up on bobbins at a surface speed of 18 m/min.

TABLE 5

| Composition Extrusion | Temp | T | E | M | dpf |
| --- | --- | --- | --- | --- | --- |
| 25% corn starch 75% copolyester | 180 C. | .015 | 859 | .02 | 32 |
| 50% corn starch 50% copolyester | 150 C. | .015 | 396 | .13 | 68 |
| 75% corn starch 25% copolyester | 220 C. | Would not extrude | | | |

Loops of continuous extruded fiber (about 4 inches in diameter and weighting about 5 g) were marked by sandwiching a portion of the loop between two (1/16 inch thick, 1 inch square) polytetrafluroethylene washers bolted together. After 4 weeks of exposure in the rotary composter described in Example 1, all the fiber outside the washers had disappeared with the 50% starch sample. There was only a small residue of fiber remaining outside the washers with the 25% starch sample.

EXAMPLE 6

This demonstrates the preparation of fibers containing 5% corn starch or 5% rice starch and evaluation of their performance under hydrolysis conditions.

Two polymer blends were made using the same polymer in Example 4, samples 4A–4D. Blend 6A was made with 5% corn starch and blend 6B was made with 5% rice starch by the procedure detailed in Example 1. The fragmented polymer blends were dried in a 75 C. vacuum oven for two days and molded into ½ inch diameter rods in a heated mold. The rods were melted and spun through a spinneret with five 0.015" diameter ×0.045" long holes through a filter pack having screens with the following mesh sizes, 50/100/200/350/50, at a spinneret temperature of 180 C., and a delivery rate of about 0.5 cc/min onto a takeup roll running at a surface speed of 40 m/min, over a (half inch diameter) pin heated internally to 50 C., and onto a set of canted draw rolls running at a surface speed of 80 m/min. and then onto a windup bobbin.

The tensile properties of both these fibers and of a control fiber spun from the same polymer without any starch addition are given in Table 6 below. Samples of all three fibers were boiled for 2 and 4 hrs in deionized water and their molecular weights were determined by gpc and are also given in Table 6.

TABLE 6

| Composition | T | E | M | To | Init | Mn 2 hr | 4 hr |
| --- | --- | --- | --- | --- | --- | --- | --- |
| 5% corn starch | .5 | 240 | 2.3 | .6 | 37770 | 7400 | 6240 |
| 5% rice starch | .5 | 199 | 4.1 | .5 | 33800 | 7230 | 5720* |
| 0 starch | .5 | 688 | 2.1 | 1.3 | 37340 | 10340 | 6520 |

*This fiber had disintegrated to a powder at the end of the 4 hour hydrolysis test.

Example 7

This shows the preparation of starch/copolyester and starch/copolyester/biodegradable additive compositions continuously in a twin screw extruder, injection molding of some of the compositions and their evaluation in composting.

Copolyester Resin Preparation

Polymers having the following compositions were prepared in the same reactor and by procedures similar to those in Example 1 herein

| Polymer 1 (mp 176 C.) | Polymer 2 (mp 175 C.) |
| --- | --- |
| 73% T | 68% T |
| 25% 5 | 30% 5 |

| Polymer 1 (mp 176 C.) | Polymer 2 (mp 175 C.) |
|---|---|
| 2% 5SI | 2% 5SI |
| 90% 2G | 100% 2G |
| 10% DEG | |

The polymer pellets were dried overnight in a large tray dryer at 80° C. with hot dry air recirculation to a moisture content of less than 0.04%.

Corn starch (Corn Products 3005 from CPC International, Inc.), and rice starch (Sigma Chemicals catalogue #S7260) were dried overnight in a large tray vacuum oven at 90° C. and less than 1 mm Hg vacuum to a moisture content of less than 1%, and stored in sealed containers until used.

Polyethylene adipate (RUCOFLEX® S-101-55, nominal molecular weight=2000, from Ruco Polymer Corporation) was used directly without pretreatment.

Blends of polymer pellets and starch were made by manually tumbling the materials in plastic bags. The dry (room temperature) starch was added to warm polymer pellets from the dryer, and the (still warm) mixture fed to the extruder. When polyethylene adipate (RUCOFLEX®) was used, the polymer and RUCOFLEX® were blended first to assure uniform distribution of RUCOFLEX® in the warm polymer, prior to addition of the starch.

The following compositions were made:-
7A 60% polymer 1, 40% cornstarch
7B 60% polymer 1, 40% rice starch
7C 55% polymer 1, 40% cornstarch, 5% RUCOFLEX®
7D 60% polymer 2, 40% cornstarch
7E 60% polymer 2, 40% rice starch
7F 55% polymer 2, 40% rice starch, 5% RUCOFLEX®

The blends were placed in the feed hopper (with nitrogen purge) of a K-tron twin screw feeder (Model #T-35 with #6300 controller) and metered to a Werner and Pfleiderer ZSK 30 mm twin screw extruder. This extruder had an L/D of 30/1 with a vacuum port and a mild mixing screw. The temperature of the extruder barrel was electrically heated from 165° C. at the feed end of the extruder to 190° C. at the discharge. The extruder was operated at 150 RPM, and the vacuum port was connected to house vacuum and the vacuum permitted to fluctuate with process conditions. A single hole die (⅛ inch dia.) was used for discharge. The resulting strand was quenched in a 6 ft long water trough, dewatered with an air knife and cut into pellets with a Conair cutter (Model #304). Specific operating conditions for the individual compositions are listed below.

| Comp. | Feed Rate PPH | Screw Torque % max | Die Pressure PSIG | Melt Temp C. | Vacuum in Hg | COMMENT |
|---|---|---|---|---|---|---|
| A | 34 | 58 | 800 | 251 | 13 | ROUGH STRAND BUT FEW BREAKS |
| B | 32 | 60 | 800 | 248 | 13 | ROUGH STRANDS WITH MANY BREAKS |
| C | 31 | 52 | 750 | 241 | 12 | SMOOTH STRAND NO BREAKS |
| D | 33 | 56 | 750 | 253 | 13.5 | ROUGH STRANDS BUT FEW BREAKS |
| E | 33 | 53 | 760 | 250 | 13.5 | ROUGH STRANDS WITH MANY BREAKS |
| F | 29 | 53 | 560 | 240 | 13 | SMOOTH STRANDS NO BREAKS |

The RUCOFLEX® lowers die pressure and melt temperature, while improving strand surface smoothness. Samples A, B, D, and E were stiff and brittle while samples C and F were flexible and tough, showing the advantage of using the RUCOFLEX®.

To show the dimensional stability of these compositions in aqueous environments, a piece of the extrudate from composition D was immersed in room temperature water for 91 hrs. It showed a 1.2% gain in weight, a 4.7% increase in diameter and a 1% loss in length.

Composition C and F pellets were dried overnight in a large tray drier at 80° C. with hot dry air recirculation. Each composition was injection molded, using a 6 oz Van Dorn injection molding machine with the following characteristics;

Model 125-RS-6
125 ton clamping pressure
General purpose 1.575 inch screw
Hydraulic gauge factor 10.7/1

A mold designed to produce two 5"×½"×⅛" standard Izod bars and one 3"×5"×1/16" plaque was attached.

The extruder heater temperature was set at 200° C. and the mold was cooled to 20° to 25° C. The injection cycle used was −1 second boost (1200 psig), 30 seconds inject (600 psig), 15 second hold (0 psig). Ram speed was operated at maximum, screw speed was 60 RPM, and screw back pressure was 50 psig.

Properties of the bars and plaques with compositions C and F, conditioned and measured at 23 C. and 50% RH, are in the following Table:

| Sample | Yield Stress (KPSI) | Maximum Stress (KPSI) | Break Stress (KPSI) | Yield Elongation (%) | Ultimate Elongation (%) |
|---|---|---|---|---|---|
| C-MD | 1.74 | 1.8 | 1.03 | 16 | 77 |
| C-XD | 2.0 | 2.0 | 1.4 | 8.9 | 96 |
| F-MD | 1.74 | 1.83 | 1.5 | 10 | 35 |
| F-XD | 1.94 | 1.98 | 1.79 | 8.9 | 37 |

| Sample | Izod Impact (FTLB/IN) |
|---|---|
| C-at gate | 0.44 |
| C-far edge | 0.46 |
| F-at gate | 0.35 |
| F-far edge | 0.33 |

One plaque and one tensile bar of compositions C and F were placed in a rotary composter (Kemp Compostumbler) with a mixture of 50% municipal solid waste and 50% municipal waste water treatment sludge and allowed to compost for 28 days, turning every week and adding water after two weeks to maintain greater than 40% moisture. The composition C plaque and bar broke into fragments during this treatment.

The composition F plaque and bar were substantially intact but all the samples could easily be broken by bending. Gpc analysis of the polyester showed a 31% reduction in Mn for the Composition C bar and a 10% Mn reduction for the composition F bar. Samples recovered from a 28 day compost test were subjected to a second 28 day test, from which no samples remained in condition to be recovered.

EXAMPLE 8

This shows the preparation of extruded films and porous, liquid water-impermeable films from blends of corn starch and a plasticizer with two 5SI-containing copolyesters.

Polymers with compositions: 2G/DEG(90/10)-T/5/5SI(78/20/2) (Polymer 8A) and 2G/DEG/PEG(Mw=600)(85/8/7)-T/5/5SI(86.2/12/1.8) (Polymer 8B) were blended with corn starch and polyethylene adipate (Rucoflex ® S-101 Mn=2000) by the procedure given in Example 7 to yield pellets having the following compositions:

Composition A: 49.7% Polymer 8A+46.7% corn starch+3.6% Rucoflex ®
Composition B: 81.1% Polymer 8B+17.5% corn starch+1.4% Rucoflex ®

The pellets were dried overnight at 80° C. in a recirculating desiccated-air oven. The dried resin was placed in the hopper of a single screw volumetric feeder (K-tron, Model No 7) from which it free falls to the inlet of a 28 mm Werner and Pfleiderer twin screw extruder with a vacuum port (maintained at house vacuum) attached to a 10 inch wide film die with about a 0.010 inch gap. A dry nitrogen purge was maintained in the feed hopper and the feed throat of the extruder. The extruder was operated at 150 RPM screw speed with a heater temperature (°C.) profile of

|  | Zone 1 | Zone 2 | Zone 3 | Zone 4 | Zone 5 | Die | Melt |
|---|---|---|---|---|---|---|---|
| Comp. A | 130 | 140 | 150 | 170 | 170 | 160 | 195 |
| Comp. B | 180 | 190 | 200 | 220 | 220 | 200 | 231 |

The extruded polymer films were electrostatically pinned on an 8 inch diameter smooth quench drum maintained at 26 C. with cold water and collected on release paper using a standard tension roll. The quench drum speed was adjusted from 5 to 15 ft per minute to obtain film samples from about 8 mils to 1.5 mils thick. These films could be drawn over a 55 C. hot pin, to give whitened films.

| Comp. | As Extruded Thick. (mil) | Draw Ratio | Width Red'n | Drawn Thick. (mil) |
|---|---|---|---|---|
| A | 4 | 4X | 33% | 2.5 |
| B | 1.5 | 2.8X | 37% | 1.5 |

The relative densities of the drawn films were calculated to be about 0.6 those of the undrawn films. Porosity was developed by the drawing process.

When samples of these films were sealed to the bottom of a piece of glass tubing which was then filled with a 15 cm deep layer of deionized water, no water penetration was noted over a period of 30 min. This indicates that the films have utility for use as barriers to liquid water penetration, despite their porosity and the presence of starch in the films.

What is claimed is:

1. A fiber and film forming blend of starch, in amount by weight 1 to 80%, and of a polyester, in amount by weight 99 to 20%, wherein said polyester consists essentially of recurring structural units of the formulae:

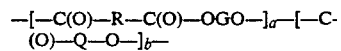

wherein up to about 40 mole % of R is selected from the group consisting of a chemical bond and one or more divalent, non-aromatic, $C_1$–$C_{10}$ hydrocarbylene radicals, and the remainder of R is at least about 85 mole % p-phenylene radical,
   wherein G is up to about 30 mole % of a polyethylene ether radical selected from the group consisting of

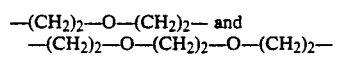

and the remainder of G is selected from the group consisting of polyalkylene ether radicals of molecular weight at least about 250, and —$(CH_2)_2$—, —$(CH_2)_3$—, and —$(CH_2)_4$— radicals,
   wherein Q is derived from an hydroxy acid of formula

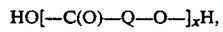

where x is an integer, such hydroxy acid having a melting point at least 5° C. below its decomposition temperature, and Q is selected from the group consisting of a chemical bond and hydrocarbylene radicals —$(CH_2)_n$—, where n is an integer from 1 to 5, —C(R')H—, and —C(R')HCH$_2$—, wherein R' is selected from the group of —CH$_3$ and —CH$_2$CH$_3$,
   and wherein "a" and "b" are mole fractions of the polymer, and the mole fraction "a" may be 0.6 to 1 and, correspondingly, mole fraction "b" may be 0 to 0.4,
   and wherein about 0.1 to about 15 mole % of the polymer contains alkali metal or alkaline earth metal sulfo groups.

2. A blend according to claim 1, containing, by weight, 5 to 70% of starch and complementally 30 to 95% of said polyester.

3. A blend according to claim 1 or 2, wherein about 0.1 to about 2.5 mole % of the polyester contains alkali metal or alkaline earth metal sulfo groups.

4. A fiber of the blend of claim 1 or 2.

5. A non-woven sheet of the blend of claim 1 or 2.

6. A film of the blend of claim 1 or 2.

7. A foam of the blend of claim 1 or 2.

8. A composite of the film of claim 6 and of a layer of nonwoven sheet or of paper.

9. A disposable diaper which includes an absorbent body portion having on one surface thereof a water permeable sheet of the blend of claim 1 or 2.

10. A disposable diaper which includes an absorbent body portion having on one surface thereof a water impermeable sheet of the blend of claim 1 or 2.

* * * * *